United States Patent
Tsang et al.

(10) Patent No.: US 7,381,547 B2
(45) Date of Patent: Jun. 3, 2008

(54) METHODS AND COMPOSITIONS TO DETECT BACTERIA USING MULTIPLEX PCR

(75) Inventors: Tat-Kin Tsang, Winnetka, IL (US); Xiangwen Meng, Skokie, IL (US); Hongjun Zhang, Glenview, IL (US)

(73) Assignee: Tzam Diagnostics, LLC, Wilmette, IL (US)

( * ) Notice: Subject to any disclaimer, the term of this patent is extended or adjusted under 35 U.S.C. 154(b) by 297 days.

(21) Appl. No.: 10/834,151

(22) Filed: Apr. 28, 2004

(65) Prior Publication Data

US 2005/0244836 A1 Nov. 3, 2005

(51) Int. Cl.
*C12P 19/34* (2006.01)
*C12Q 1/68* (2006.01)

(52) U.S. Cl. .......................... 435/91.2; 435/6
(58) Field of Classification Search ............ None
See application file for complete search history.

(56) References Cited

U.S. PATENT DOCUMENTS

2002/0168726 A1* 11/2002 Bolin et al. ............... 435/69.3
2004/0052799 A1* 3/2004 Smith et al. ............. 424/184.1

OTHER PUBLICATIONS

Meng, et al. (Digestive Disease Week Abstracts and Itinerary Planner, 2003, vol. 2003, Abstract No. S1217).*
Monstein and Jonassen (Biochemical and Biophysical Research Communication, 2001, vol. 285, p. 530-536).*
Monstein and Ellnebo-Svedlund (Helicobacter, 2002, vol. 7, No. 5, p. 287-296).*
Kawamata et al. (1996, Biochemical and Biophysical Research Communications, vol. 219, p. 266-272).*
Muller et al. (Biological Research, 2002, vol. 35, No. 1., p. 1-19), obtained from World Wide Web: <http://www.scielo.cl/scielo.php?script=sci_arttext&pid=S0716-97602002000100010 &Ing=en &nrm=iso>. ISSN 0716-9760.*
Sequence alignments, pp. 1-8.*
Koehler et al. (Journal of Clinical Pathology, Feb. 2003, vol. 56, p. 36-42).*
Mues et al. (Agilent publication # 5989-0078EN, published Oct. 1, 2003, p. 1-4).*
Buck et al. (Biotechniques, 1999, 23(5), p. 528-536).*
Bertolini et al. (Phytopathology, 2003, vol. 93, No. 3, p. 286-292).*
Meng, Xiangwen et al. "Comparison of a novel multiplez PCR assay and CLOtest test for the diagnosis of *H pylori*" Evanston Northwestern Healthcare Research Institute.
Meng, Xiangwen et al. "Comparison of a novel multiplez PCR and histology method for the diagnosis of *H. pylori*" Evanston Northwestern Healthcare Research Institute.

(Continued)

*Primary Examiner*—Gary Benzion
*Assistant Examiner*—Stephanie K Mummert
(74) *Attorney, Agent, or Firm*—Barnes & Thornburg LLP; Alice O. Martin

(57) ABSTRACT

Multiplex polymerase chain reaction assays for detecting a bacteria (e.g. *Helicobacter pylori*) in a specimen use multiple oligonucleotide primer pairs based on the sequences of multiple loci of the bacteria. In one application, up to five loci in the genomic DNA sequences of *Helicobacter pylori* were amplified. Two fragments of *H. pylori* were amplified from each locus, wherein a second fragment was an internal fragment of the first fragment.

18 Claims, 7 Drawing Sheets

OTHER PUBLICATIONS

Meng, Xiangwen et al. "Identification of *Helicobacter pylori* DNA from food sources by a novel multiplex PCR assay" *Evanston Northwestern Healthcare Research Institute*.

Meng, Xiangwen et al. "A novel multiplex PCR assay for Detection of *Helicobacter pylori*" *Evanston Northwestern Healthcare Research Institute*.

AGA Poster Session "Diagnosis of *H. pylori* infection" *Orange County Convenstion Center*.

Website: http://home.coqui.net/myrna/heli.htm "*Helicobacter pylori*: gastritis and ulcers in children" printed Mar. 19, 2004: pp. 1-3.

Roma-Giannikou E et al. (2003) "Intrafamilial spread of *Helicobacter pylori*: a genetic analysis" *Helicobacter* Feb.; 8(1):15-20.

Koehler CI et al. (2003) "*Helicobacter pylori* genotyping in gastric adenocarcinoma and MALT lymphoma by multiplex PCR analysis of paraffin wax embedded tissues" *Mol Pathol* Feb.; 56(1):36-42.

Monstein HJ and Ellnebo-Svedlund K (2002) Molecular typing of *Helicobacter pylori* by virulence-gene based multiplex PCR and RT-PCR analysis. *Helicobacter* October; 7(5):287-96.

Chisholm SA et al. Determination of *Helicobacter pylori* vacA allelic types by single-step multiplex PCR. Laboratory of Enteric Pathogens, Central Public Health Laboratory, London, UK.

Ergun O et al (2002) "Does colonization of *Helicobacter pylori* in the heterotopic gastric mucosa play a role in bleeding of Meckel's diverticulum?" *J. Pediatr Surg.* Nov.; 37(11):1540-1542.

Monstein et al., "Differential Virulence-Gene mRNA Expression In Coccoid Forms of *Helicobacter pylori*," Biochem. & Biophys. Res. Comm., 285, 530-536 (2001).

International Search Report issued in PCT/US05/14389.

Cousins et al., "Use of polymerase Chain Reaction for rapid detection of tuberculosis," *J. Clin. Micro.*, vol. 35 (1): 255-258 (2002).

International Search Report issued in PCT/US05/14389 (2006).

* cited by examiner (A)

(B)

(A)

(B)

(A) 0.86kb fragment (including ureC and prfA gene)

706 bp catatagccgcttttctggtgtctttaccgattagaattttattcgtttgagaatgttttttaaaata
caatccggcagcaatgcctaaacgcatcacaaacatggggtgagtttcacccctgctttacc**cctcac
gccatcagtcccaaaaat**ttttcatcgttataaaatacctttaaactattttaatcaattttagata
gaattatgccaaattttacattacaaagggattaaaacaaggctatggcaaatcataagtccgcagaaa
agcgaatcagacagaccattaagagaaccgaacgcaacaggttctataaaactaaaattaaaaatatca
ttaaagccgtgcgtgaagccgttgctgtcaatgatgtagcaaaagctcaagagcgtttgaaaatcgcta
ataaagagttgcataaatttgtcagcaaggggatttaaagaaaaacaccgcttctaggaaagtctcaa
ggcttaacgcttcagtgaaaaaaatcgctctcgcttagttttgtggcgttttcaacttctttaagctca
gtaatgggttttattattgggcttctttttaagttttgcgttttttagattgttgtatttttattca
catcttttataggtagtctcgcatgtccattctagccgaaaagctttcttccattctcaaa**cgatacg
acgaactcacggcgtt**

(B) ure A

526 bp gatgtgtgtgtcaataccaccagcagttacgatcaaaccttcaccggctaaggcttcagta**gcaggacc
tacgctaagattgt**ttttaacgccatcttgcatgtctttgttaccgcctttaccaatgccagcgatttt
gccatctttaataccaatatccgctttataaataccggtgtaatccacgattaaagcgttagtgatgat
tagatccaattcttctttgctagggttgttggattggctcatgccttctctcagggttttaccgccacc
gaatttaagctcttcgccataaatggtgtagtcatgttctacttcagcgatcaagtctgtatcgcccaa
tctcactttatcgcctgtagtagggccatacatagaaacatattcttttctgctaatcttttcatttc
ttactccttaattgttttacatagttgtcatcgcttttagcgccatgaaaaccacgctctttagctct
gtgtaaagcaattttttttgctttcgttgtctgcttgcctatca

FIG. 7 (A-B)

(C) 16S rRNA

370 bp acgggaggcagcagtagggaata**ttgctcaatgggggaaaccctgaagcagcaacgccgcgtggaggat
gaaggt**tttaggattgtaaactccttttgttagagaagataatgacggtatctaacgaataagcaccgg
ctaactccgtgccagcagccgcggtaatacggagggtgcaagcgttactcggaatcactgggcgtaaag
agcgcgtaggcgggatagtcagtcaggtgtgaaatcctatggcttaaccatagaactgcatttgaaact
actattctagagtgtgggagaggtaggtggaattcttggtgtaggggtaaaatccgtagagatcaagag
gaatactcattgcgaaggcgacctg

(D) 26kDa (including tsaA)

277 bp gtagaaaaaggcggtattggtcaagtaactttccctatggtggctgatattaccaaaagcatttctaga
gactatgatgtgttgtttgaagaagcgatcgctttgagaggagcttttttgattgacaaaaacatgaaa
gtaaggcatgcggtgatcaatgacttaccattaggcagaaatgcagatgaaatgcttcgcatggtggac
gctctcttacactttgaagaacatggtgaagtttgcccagcaggtt**ggagaaaaggcgataaaggcatg
a**

(E) hpA

138 bp atccgttcccttaaccatag<u>tgctaactaaccccccgctatggc</u>ttgaatgggtggttttaagaattt
ttcttgaatgtccaactcgctcaaatccatcgtaaagaatccaaagattccccactcataggctctag

FIG. 7 (C-E)

METHODS AND COMPOSITIONS TO DETECT BACTERIA USING MULTIPLEX PCR

BACKGROUND

Microorganisms such as bacteria and viruses cause serious infectious diseases such as tuberculosis, cholera, hepatitis and meningitis. To diagnose and cure bacterial infections requires rapid and early identification of specific disease causing pathogens in clinical specimens. Several bacterial infections do not show characteristic symptoms initially, which requires sensitive and specific tools to diagnose infections.

*Helicobacter pylori* infection is one of the most common bacterial infections in humans. The prevalence of *H. pylori* infection is worldwide and may be as high as 80% in developing countries and up to 40% in developed countries. However, the mode of transmission, the natural history, and other aspects of the epidemiology of *H. pylori* infection are still unclear. Presence of *Helicobacter pylori* bacteria in gastric mucosa and epithelia may be associated with chronic gastritis, peptic and duodenal ulcers, and gastric cancers.

Detection of *H. pylori* is generally accomplished in two ways: (1) directly, by examining a stomach biopsy by histology, cell culture, and other methods to analyze tissue specimens; or (2) indirectly, by testing a sample of peripheral blood serum for circulating antibodies against *H. pylori*. Some methods require endoscopy with a biopsy. Direct detection methods currently available for *H. pylori*, include bacterial culture, histology, serology, stool antigen test, rapid urease test (*Campylobacter*-like organism or CLOtest), isotope urease breath test, and conventional polymerase chain reaction (PCR).

The PCR based methods are sensitive and specific when compared to the urease assay in the presence of other urease-positive bacteria. PCR based methods are relatively inexpensive and produce results faster than bacterial culture, because culturing *H. pylori* is lengthy and is not possible in many situations. Conventional PCR generally uses a set of primers to amplify a genetic region in *H. pylori*. PCR tests for various bacteria, including *H. pylori*, are available for a broad spectrum of specimens, including laboratory cultures and clinical samples. Although conventional PCR based detection methods have many advantages, there are some disadvantages due to both frequent false-positive and false-negative results. The presence of polymorphisms at the primers' binding sites may lead to low specificity in conventional PCR tests.

SUMMARY OF THE DISCLOSURE

A novel one-step multiplex polymerase chain reaction detection system using a plurality of genetic loci was developed to identify a pathogenic bacteria present in clinical specimens. In one application, up to five loci in the genomic DNA sequences of *Helicobacter pylori* were chosen as amplification targets. Two fragments of *H. pylori* were amplified from each locus, wherein a second fragment was an internal fragment of the first fragment.

A method of detecting a bacteria in a specimen includes the steps of:
(a) performing a multiplex polymerase chain reaction, wherein a plurality of DNA fragments representing a plurality of loci in the bacteria are amplified by a plurality of primers, where for each pair of forward and reverse primers, one primer is internal to the other; and
(b) determining that a specimen is positive for the bacteria if a number of amplified fragments is sufficient to detect the bacteria from other bacteria.

The primers used to amplify multiple loci in a bacteria include the following characteristics:
(a) are about twenty to thirty bases long;
(b) have a melting temperature of about 60° C.;
(c) have a GC content of about fifty percent;
(d) have minimal dimer formation; and
(e) have low frequency of mutations in the primer binding site.

The multiplex polymerase chain reaction is performed with an isolated bacterial DNA, wherein the bacterial DNA is isolated from a clinical sample. The clinical sample is selected from a group of gastrointestinal tract tissue, stool, urine, blood, saliva, mucus secretions, dental plaque, and other tissues capable of containing the bacteria. The multiplex polymerase chain reaction is also suitably performed directly on a biological sample or a specimen.

A diagnostic kit to detect a pathogenic bacteria in a specimen includes in discrete containers:
(a) a plurality of primers to amplify a plurality of DNA fragments from the bacterial genomic sequence; and
(b) reagents to perform a multiplex polymerase chain reaction.

The diagnostic kit to detect the bacteria also includes a DNA polymerase, nucleotides, and buffers. The plurality of primers in the diagnostic kit are capable of amplifying a plurality of DNA fragments so that half of the amplified fragments are internal to the other half of the amplified fragments.

A method for detecting *Helicobacter pylori* in a specimen includes the steps of:
(a) performing a multiplex polymerase chain reaction, wherein a first set of primers amplifies a first set of DNA fragments from a *Helicobacter pylori* genomic sequence and a second set of primers amplifies a second set of DNA fragments from the *Helicobacter pylori* genomic sequence that are internal to the first set of DNA fragments; and
(b) determining that a specimen is positive for *Helicobacter pylori* if at least fifty percent of all the fragments or at least two fragments representing either the first set or the second set of DNA fragments and the corresponding internal fragments are amplified.

A method for detecting *Helicobacter pylori* in a specimen includes the steps of:
(a) performing a multiplex polymerase chain reaction, wherein
  (i) a first DNA fragment from a *Helicobacter pylori* genomic sequence is amplified by a first primer pair and an internal segment of the first DNA fragment is amplified by a second primer pair,
  (ii) a second DNA fragment from a *Helicobacter pylori* genomic sequence is amplified by a third primer pair and an internal segment of the second DNA fragment is amplified by a fourth primer pair; and
(b) determining that a specimen is positive for *Helicobacter pylori* if at least one of the fragments and its internal fragment or fifty percent of all the fragments are amplified.

A multiplex polymerase chain reaction with the first set of primers was performed separately from the multiplex polymerase chain reaction with the second set of primers. The first set of primers and the second set of primers amplified a total of ten fragments representing five loci in the *Helicobacter pylori* sequence.

The *Helicobacter pylori* locus is selected from a group of coding, non-coding, exons, introns, and regulatory regions. A plurality of loci to be amplified was selected from a group of DNA sequences that include a 0.86 kb DNA fragment, Urea A gene, 16S rRNA, a DNA sequence encoding a 26 kDa antigen, and Hpa A gene, whose nucleotide sequences are listed in FIG. 7. A plurality of primers used to amplify the loci was selected from a group of primers whose DNA sequences are listed in TABLE 2. The primer pairs used to amplify multiple loci in *H. pylori* are designed from a group of DNA sequences comprising a 0.86 kb DNA fragment, Urea A gene, 16S rRNA, a DNA sequence encoding a 26 kDa antigen, and Hpa A gene, whose nucleotide sequences are listed in FIG. 7.

In a multiplex PCR disclosed herein, the first primer pair and the second primer pair have a common primer per locus. The primer pairs were selected from the primers listed in TABLE 2. A multiplex polymerase chain reaction to detect *Helicobacter pylori* was performed, wherein up to ten DNA fragments representing five *H. pylori* loci were amplified by fifteen primers, the ten DNA fragments representing five internal fragments. A set of fifteen primers comprise five forward and ten reverse primers.

A method of detecting *Helicobacter pylori* in a specimen includes the steps of:
(a) designing a plurality of primers in a plurality loci of *Helicobacter pylori*, wherein the primers
    (i) are specific for *Helicobacter pylori*;
    (ii) have a low frequency of mutations in primer binding sites;
(b) performing a multiplex polymerase chain reaction wherein the plurality of primers amplify a plurality of DNA fragments representing the plurality of loci in *Helicobacter pylori*; and
(c) determining that a specimen is positive for *Helicobacter pylori* if at least fifty percent of all the DNA fragments or at least four DNA fragments representing two loci in *Helicobacter pylori* are amplified or by other empirically or statistically derived criteria.

A diagnostic kit to detect *Helicobacter pylori* in a specimen includes in discrete containers:
(c) a first set of primers to amplify a first set of DNA fragments from a *Helicobacter pylori* genomic sequence;
(d) a second set of primers to amplify a second set of DNA fragments from *Helicobacter pylori* genomic sequence that are internal to the first set of DNA fragments; and
(e) reagents to perform a multiplex polymerase chain reaction.

The diagnostic kit to detect *Helicobacter pylori* also includes a DNA polymerase, deoxynucleotides, and buffers. The kit includes a set of primers whose nucleotide sequences are listed in TABLE 2. The kit may also include reagents: a buffer comprising 100 mM Tris-HCl (pH 8.3), 500 mM KCl, 16 mM $MgCl_2$, 0.01% (weight/volume) gelatin; and 10 mM of each deoxynuclotide. The concentration of primers is about 1.0 µM.

Definitions

Locus: location of a DNA sequence in a chromosome that encodes one or more products.

Multiplex PCR: A variant of conventional polymerase chain reaction that uses at least two or more primer pairs to amplify different stretches of a target DNA molecule simultaneously.

Nested PCR: A modified polymerase chain reaction that uses one or more primers ("nested") whose sequences are complementary to an internal site of a DNA molecule that has been amplified with other primers.

Oligonucleotide: single stranded DNA molecule with any length ranging from four to about 100 nucleotides.

Primers: Oligonucleotides of about 6 bp to about 50 bp in length used for initiating polymerase chain reaction.

Forward: a primer that may bind to one of the two complementary anti-parallel DNA strands.

Reverse: primer that may bind to a strand that is complementary to the strand to which the forward primer binds.

Specimen: A biological sample such as saliva, stools, urine, blood, gastric biopsy, gastrointestinal tissue, tumor cells, mucus secretions, dental plaque, and other biological tissues, meat products, food products, and environmental samples such as soil, water.

BRIEF DESCRIPTION OF THE DRAWINGS

FIG. 7 shows the DNA sequences of five different loci from *H. pylon* that were selected for multiplex PCR (SEQ ID NOS. 1-5, respectively).

DETAILED DESCRIPTION OF THE DISCLOSURE

A plurality of DNA fragments representing a plurality of loci from a bacterial genome is amplified using nested primers in a multiplex PCR reaction to positively identify the bacterial species. A plurality of DNA fragments from a specimen containing bacteria is amplified by a plurality of primers such that half of all the amplified fragments are internal to the other half.

Figure 1:
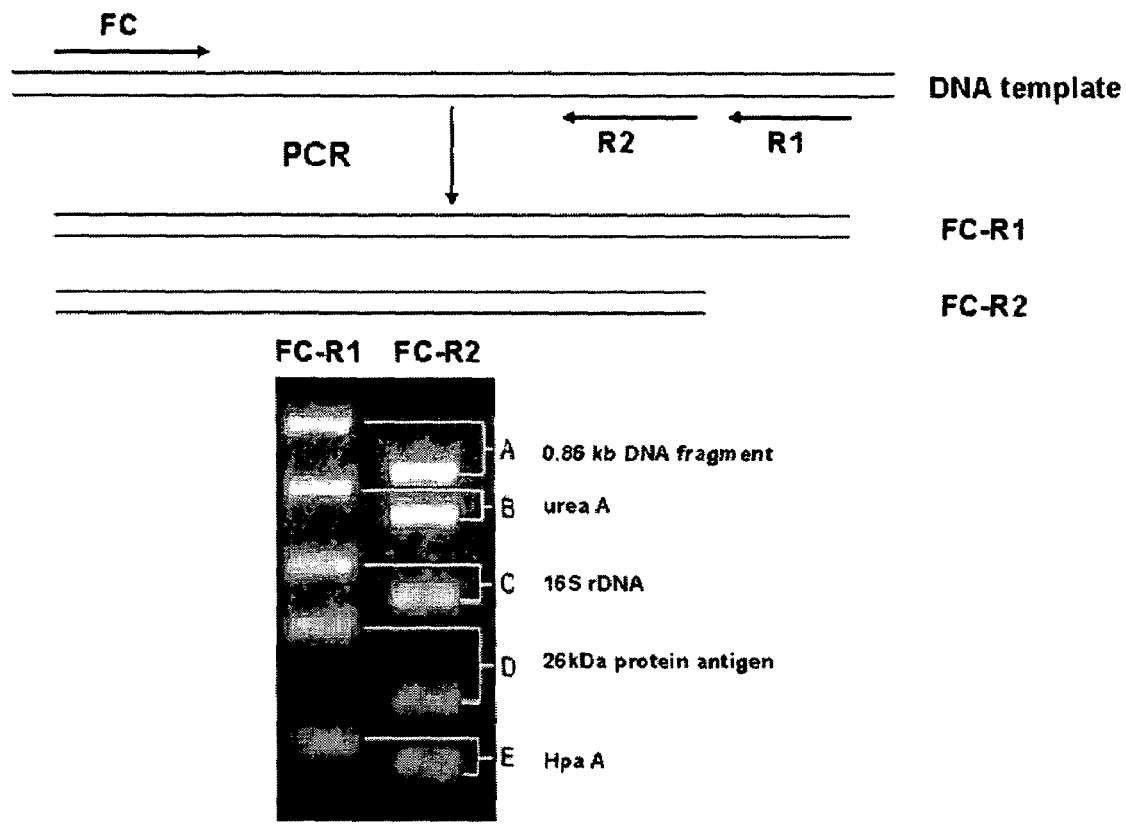
FIG. 1 is an illustration of primer design for each locus (A-E) in *H. pylori*. FC stands for forward primer, which is used as a common primer. R1 and R2 represent two reverse primers. Amplicons FC-R1 and FC-R2 represent two fragments amplified with FC and R1, FC and R2, respectively. Between the two amplified DNA fragments, one fragment is internal to the other fragment. An image of the agarose gel electrophoresis stained with ethidium bromide shows the FC-R1 and FC-R2 amplified fragments in the selected loci (A-E).

For each bacterial locus, one forward primer is selected as a common primer (FC) and two reverse primers (R1 and R2) are selected, in which R2 is inside the amplifying region of R1 (FIG. 1). In addition, these primers have the following characteristics: $T_m$, of about 60° C.; G+C: A+T, about 50%; length, 10-30 nt; minimal dimer formations with other primers; fewer mutations in the primer binding site; and are specific for a particular bacterial species.

In one example, up to five genetic loci from a bacterial genome are amplified using a set of at least five forward primers and ten reverse primers such that five of the amplified fragments are internal to the other five amplified fragments. A specimen is considered positive if at least five out of the ten amplicons are amplified or at least two of the five loci have both of their amplicons amplified. The amplified fragments can be resolved in a standard agarose gel electrophoresis or can be quantified using any other techniques such as real time quantitative PCR.

The number of loci to be selected for amplification depends on sequence similarity of a target bacterial pathogen to other commonly occurring bacteria, availability of non-conserved genomic regions in the target bacteria when compared to the commonly occurring bacteria, availability of conserved genomic regions among the various strains of the target bacterial pathogen, and technical and practical feasibility to accommodate multiple samples.

Two or more genetic loci from a bacterial genome are amplified using a set of at least two forward primers and four reverse primers such that two of the amplified fragments are internal to the other two amplified fragments.

In one example, a multiplex PCR, wherein five forward primers and five reverse primers representing five different bacterial loci are mixed to react in one reaction system and the five forward primers and five nested primers are allowed to react separately in another system. Alternatively, the five forward primers and the ten reverse primers are allowed to react in a single reaction system.

A multiplex PCR amplification was performed with isolated bacterial DNA from clinical samples that included infected tissues. A multiplex PCR amplification was performed with isolated bacterial DNA from bacterial cell cultures.

Amplifying more than one region of a nucleic acid molecule at the same time overcomes false-negative results because the possibility to amplify all or some of the selected DNA region is considerably higher when multiple regions are used rather than a single region. The amplified internal DNA fragments are helpful in minimizing false-positives. False negatives can be picked up by the one-step multiple-nested PCR. Unless the entire selected loci scanned by the multiplex PCR are deleted or mutated, the presence of some amplified fragments acts as an internal control, suggesting that the reaction has not failed, and helping rule out a false-negative result.

A standard touchdown PCR program was employed to amplify the bacterial DNA fragments. Briefly, a touchdown PCR involves decreasing the annealing temperature by 1° C. every second cycle to a 'touchdown' annealing temperature, which is then used for about 10 cycles, to optimize annealing temperatures. The basic idea is that any differences in $T_m$ between correct and incorrect annealing gives a 2-fold difference in product amount per cycle (4-fold per ° C.). Therefore, the correct product is enriched over any incorrect products.

A diagnostic kit to detect bacteria includes in discrete containers, primers, whose nucleotide sequences are determined based on the criteria described herein, a suitable DNA polymerase such as, for example, Immolase™ (Bioline, London, UK), deoxynucleotides, buffers, and optionally a set of pre-amplified bacterial DNA fragments for comparison, and a control bacterial DNA.

A diagnostic kit to detect bacteria includes a set of up to five forward primers representing up to five different bacterial loci and up to ten reverse primers (including five nested primers) representing the five loci.

Multiplex PCR was used to amplify a plurality of DNA fragments from a plurality of loci at the same time to identify *Helicobacter pylori*. Improved PCR sensitivity and specificity are due to selected amplification of various nested DNA regions. An internal control for each amplicon enhances identification of false negatives because amplification of some fragments indicates that the multiplex reaction has not failed.

Figure 2:
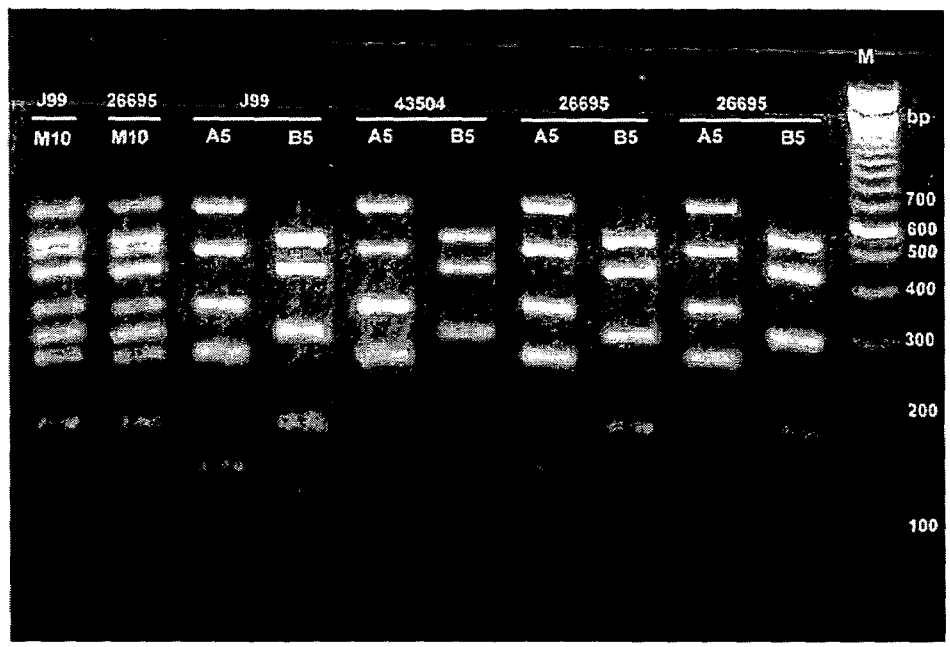
FIG. 2 shows images of agarose gel electrophoresis by which *H. pylori* is detected by a multiplex PCR method. An image of the agarose gel electrophoresis stained with ethidium bromide shows DNA bands amplified using A5 and B5 set of primers is shown in (A) and amplified using M5 set of primers is shown in (B) from various *H. pylori* strains (ATCC Nos. 43504, 26695, and J99: ATCC 700824). M10 in (A) refers to the lanes containing 10 amplified bands. M in both (A) and (B) refer to a DNA standard. A5/B5/M5 refer to lanes containing 5 DNA bands that correspond to the 5 different loci. A5/M5-1 contains 5 FC and 5 R1 primers. B5/M5-2 contains 5 FC and 5 R2 primers. M10 contains 10 primer pairs. Each locus has two bands, but in different lanes except in lane M10.
Figure 2:
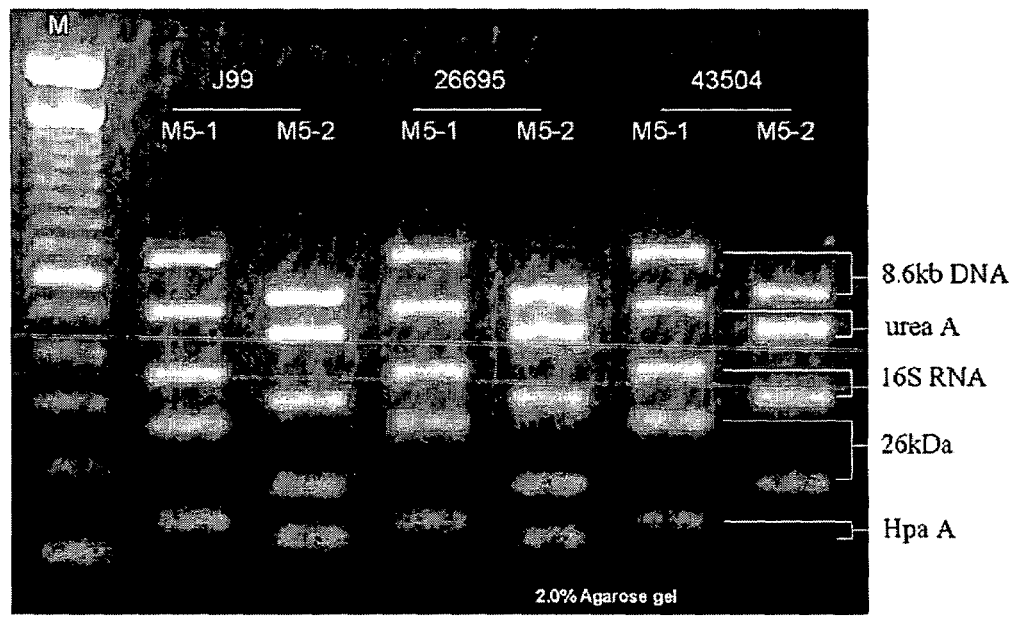
Figure 5:
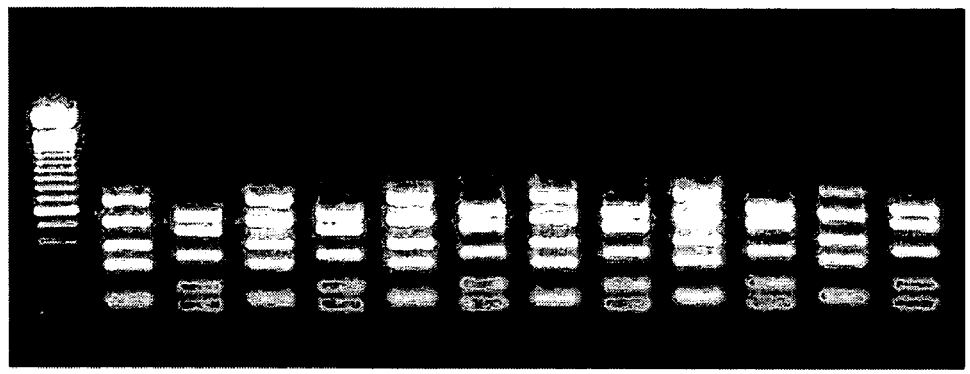
FIG. 5 shows the detection of *H. pylori* by multiplex PCR from clinical samples S1-S6 (A) and from clinical samples S7-S12 (B). M refers to a lane containing a DNA standard.
Figure 5:
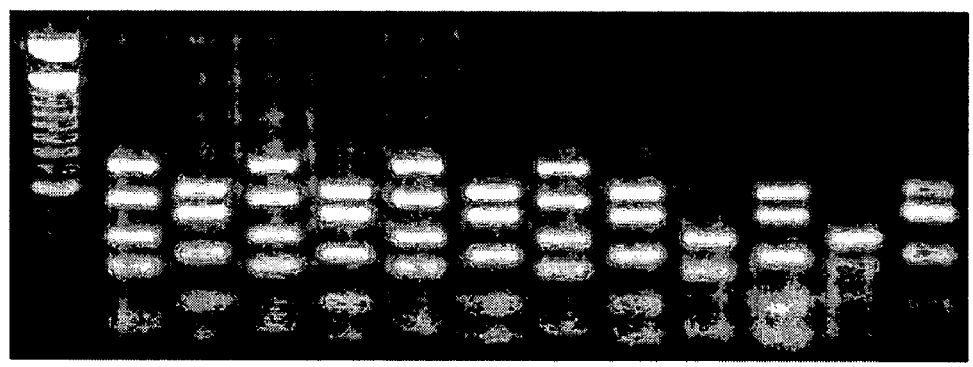
Figure 6:
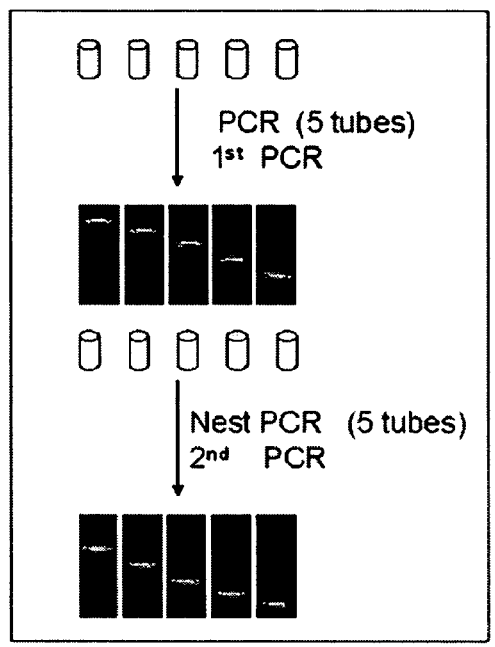
FIG. 6 is an illustration of a single primer pair PCR and a multiplex PCR (in one tube and two tubes). The illustration represents amplification from 5 different loci of *H. pylori*.
Figure 6:
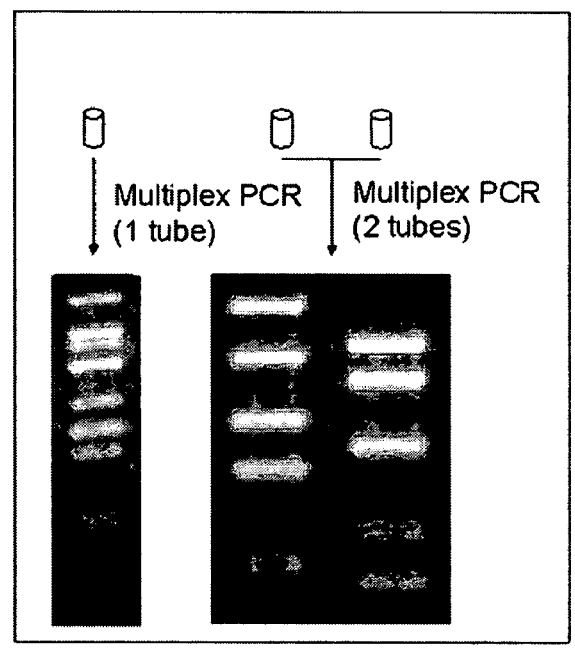

In an example of a one-step multiplex PCR detection system disclosed herein, five loci (Hpa A gene, 26 kDa protein antigen, 16S ribosomal RNA, urease A gene and a specific 0.86 kb DNA fragment) in *Helicobacter pylori*'s genome were chosen as amplification targets. For each locus, one forward primer (FC) and two reverse primers (R1 and R2) were designed such that one amplified fragment is internal to the other amplified fragment. For example, amplicon FC-R2 is internal to amplicon FC-R1 (FIG. 1). After 32-40 cycles of amplification using *Helicobacter pylori* (strains J99, ATCC No. 26695 and ATCC No. 43504) DNA as templates, 10 DNA fragments were obtained with the multiplex PCR detection system. The amplified fragments were displayed in a 2% agarose gel with ethidium bromide staining (FIG. 2). The amplified fragments correspond to the targets as follows: 0.86 kb DNA fragment, 706 bp and 574 bp; Urea A gene, 526 bp and 465 bp; 16S rRNA, 371 bp and 315 bp; 26 kDa, 277 bp and 183 bp; Hpa A gene, 138 bp and 118 bp. For direct detection of *H. pylori* from a bacterial culture, a colony was picked with a pipette tip and diluted with Tryptic Soy Broth or TE, then used as template to perform amplification directly. The ten expected DNA fragments were directly amplified from the cultures of the three standard *H. pylori* strains (FIG. 5).

Novel multiplex PCR primers were designed by reviewing several published primers that are specific for *H. pylori* genes and searching the GenBank, urease genes (ureA), 26 kDa protein antigen, Hpa A gene, 0.86 kb DNA fragment, and DNA sequences of 16S ribosomal RNA as amplification targets.

The 0.86 kb locus (706 bp) includes ureC and prfA genes. ureC encodes an urease protein involved in central intermediary metabolism and prfA gene encodes a peptide chain release factor RF-1 involved in protein synthesis. The ureA locus (526 bp) encodes an urease protein involved in central intermediary metabolism and responsible for urease activity. The 16S rRNA locus (370 bp) is a gene encoding 16S ribosomal RNA. The 26 kDa locus (277 bp) includes tsaA gene that encodes alkyl hydroperoxide reductase involved in cellular processes such as detoxification. The hpA locus (138 bp) includes hpaA gene that encodes a flagellar sheath adhesin involved in cellular processes such as chemotaxis and motility. An exemplary genomic sequence of *H. pylori* 26695 can be acquired from GenBank database with accession number AE000511.1.

For each *H. pylori* locus, a forward primer was selected as the common primer (FC) and two reversed primers (R1 and R2) were selected, in which R2 is inside the amplifying region of R1 (FIG. 1). In addition, these primers met the following criteria:

(b) Tm, around 60° C.
(c) G+C: A+T, about 50%;
(d) length, 10-30 nt;
(e) minimal dimer formations with other primers;
(f) fewer mutations in the primer binding site after checking the published *H. pylori* DNA sequences, and
(g) were specific for *H. pylori*.

To balance the primer mixture, in an embodiment, all primers were divided partitioned in two ways: a system in which all the primers were mixed together (system 1), and system 2 where five forward primers were mixed with either one set of reverse primers (system 2) separately (FIG. 7). System 1 amplified 10 DNA fragments in each tube at the same time, wherein system 2 amplified 5 DNA fragments in each tube.

Two or more genetic loci from *H. pylori* genome were amplified using a set of at least two forward primers and four reverse primers such that two of the amplified fragments are internal to the other two amplified fragments. For example, for the Ure A gene loci of *H. pylori*, a forward primer and two reverse primers are used to amplify a 526 bp and a 465 bp fragments respectively (TABLE 2). For the Hpa A gene loci, a forward primer and two reverse primers are used to amplify a 138 bp and a 118 bp fragments respectively (TABLE 2). A specimen is considered positive for *H. pylori* if at least the 526 bp fragment and its internal 465 bp fragment is present (in the case of Urea A gene) or the 138 bp fragment and its internal 118 bp fragment is present (in the case of Hpa A gene) or at least one fragment from the Urea A gene loci and at least one fragment from the Hpa A gene loci are present.

Up to five genetic loci from *H. pylori* genome were amplified using a set of at least five forward primers and ten reverse primers such that five of the amplified fragments are internal to the other five amplified fragments (TABLE 2). A specimen is considered positive for *H. pylori* if at least five out of the ten amplicons illustrated in TABLE 2 are amplified or at least two of the five loci have both of their amplicons amplified (for example, the 526 bp fragment and its internal 465 bp of the Urea A gene and the 138 bp fragment and its internal 118 bp fragment of the Hpa A gene).

A multiplex PCR, wherein the five forward primers and the five reverse primers (R1-R5) were mixed to react in one reaction system and the five forward primers and the five nested primers (RN1-RN5) were allowed to react separately in another system (TABLE 2 and FIG. 7).

A multiplex PCR amplification was performed with isolated *H. pylori* DNA from clinical samples that included gastric biopsies and from bacterial cell cultures.

A diagnostic kit to detect *H. pylori* includes in discrete containers, primers, whose nucleotide sequences are described in TABLE 2, a suitable DNA polymerase such as, for example, Immolase™ (Bioline, London, UK), deoxynucleotides, buffers, and optionally a set of pre-amplified *H. pylori* fragments for comparison, and a control *H. pylori* DNA. The diagnostic kit may also include a set of up to five forward primers representing five different *H. pylori* loci and 10 reverse primers (including 5 nested primers) representing the five loci.

In one aspect, the diagnostic kit to detect *H. pylori* includes a set of at least two forward primers representing two different *H. pylori* loci and four reverse primers (including 2 nested primers) representing the two loci.

Figure 3:
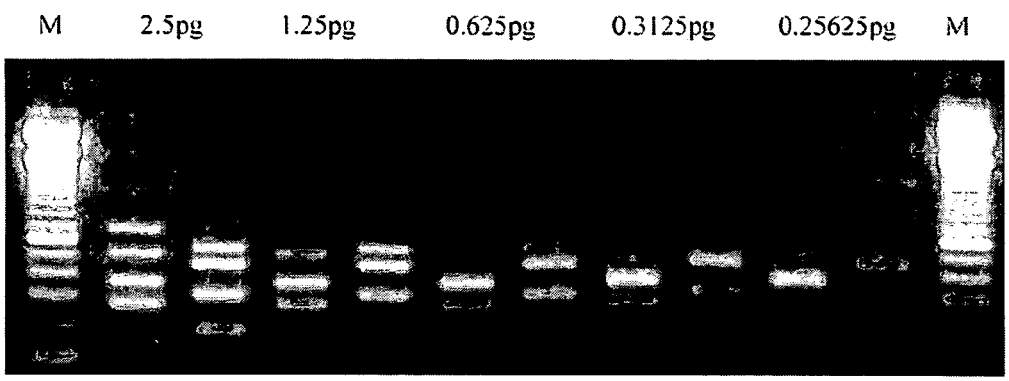
FIG. 3 is an image of the agarose gel electrophoresis stained with ethidium bromide showing the sensitivity of *H. pylori* multiplex PCR amplification system. M refers to a lane containing DNA standard and pg refers to picograms of DNA used for amplification.

The sensitivity of the one-step multiple-nested PCR assay (multiplex PCR) was investigated through a 36-40 cycle amplification of different dilutions of *H. pylori* DNA. The multiplex PCR method disclosed herein, was able to detect 10 DNA bands (in two tubes) in a single reaction when the DNA of *H. pylori* from the template was diluted to as little as 2.5 pg (FIG. 3).

Figure 4:
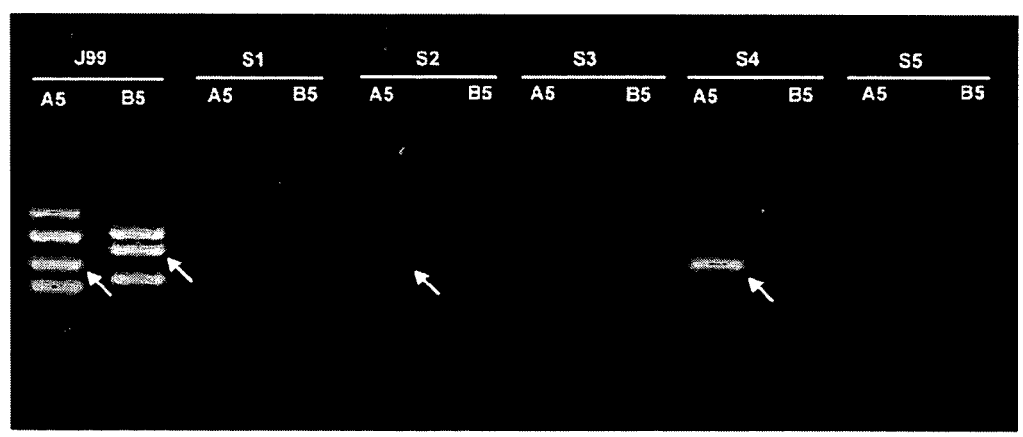
FIG. 4 is a gel picture showing the specificity of *H. pylori* multiplex PCR amplification system. S1-S5 refer to the various samples used. S1-*E. Coli*, S2-*Enterobacter aerogenes*, S3-*Enterobacter cloacae*, S4-*Enterococcus* spp, S5-Viridans group, J99-*H. pylori* (ATCC 700824). The arrows indicate the presence of the 16S rRNA.

The specificity of the one-step multiple-nested PCR assay was investigated with 11 bacterial species, using *H. pylori* J99 as a positive control. None of the sets of fragments amplified from the 11 bacterial species displayed the standard *H. pylori* J99 multiplex PCR band pattern and only 2 bacterial species *Enterobacter aerogenes* and *Enterococcus* Spp., showed one 16S rRNA band (FIG. 4).

The internal controls of the one-step multiple-nested PCR to detect *H. pylori* can minimize false-positives caused by homologous DNA sequences among various species in the primer binding sites. For example, one 16S rRNA band was generated for *Enterobacter aerogenes* and *Enterococcus* Spp. They can be distinguished from *H. pylori*, however, because both fragments from one locus and multiple loci are amplified in the case of *H. pylori* and not with the other bacterial species that were tested.

Amplified DNA fragments from a specimen containing *H. pylori* are confirmed with the one-step multiple-nested PCR because the disclosed primers produce two fragments for each of the five loci, one internal to the other. When both fragments are present for each locus, the DNA sample is inferred to be from *H. pylori*. On the contrary, if only one band is present for each locus, it may be caused by polymorphism in the amplified region.

Based on a proposal made by Monteiro et al. (2001), that a traditional PCR diagnosis for *H. pylori* is considered positive when one of two biopsied specimens from each part of the stomach is positive using two sets of primers derived from different genes, the disclosed one-step multiple-nested PCR assay was considered positive for *H. pylori* if 5/10 fragments or both DNA fragments from 2/5 loci were amplified.

To compare the sensitivity and the specificity of the multiplex PCR assays disclosed herein to some of the standard *H. pylori* tests, a comparative experimental analysis was performed. The results of multiplex PCR assays for *H. pylori* and the standard CLOtest and histological method shown in TABLE 1, indicate that the multiplex PCR system described herein is a sensitive and a specific method for identifying *H. pylori* in a clinical specimen.

EXAMPLES

Example 1

Comparison of Multiplex PCR with CLOtest for Detection of *H. pylori*

Ninety patients with dyspepsia symptoms undergoing endoscopy in Evanston Northwestern Healthcare (Evanston, Ill.) were selected. To overcome the problem of patchy *H. pylori* distribution so that the organism is not captured in the tested tissue sample, the same gastric specimen was used for both the CLOtest and PCR assay. The CLOtest was performed first following standard protocols and the results were obtained from about 20 minutes to 24 hours. The specimens were collected from the CLOtest gel, DNA was isolated, and the one-step multiplex PCR was performed.

The multiplex PCR amplification was performed for about 36-40 cycles and the amplified PCR products were detected on an agarose gel electrophoresis system. Using the standard *Helicobacter pylori* DNA as a template, 10 expected DNA fragments were obtained after amplification with the PCR method disclosed herein. On a 2% agarose gel, the following DNA fragments were displayed like two DNA ladders: a) 706 bp, 526 bp, 371 bp, 277 bp, 138 bp and b) 574 bp, 465 bp, 315 bp, 183 bp, 118 bp. For the multiplex PCR analysis, a specimen was considered positive for *H. pylori* if 5 out of 10 DNA fragments or both DNA fragments from 2 out of the 5 loci were amplified.

Positive results were obtained in 68% (61/90) with multiplex PCR and 43% (39/90) with CLOtest (TABLE 1). The sensitivity and specificity was 62% and 97% for CLOtest relative to multiplex PCR respectively (TABLE 1). The 10-primer pair-combination plus the internal control of each locus showed the multiplex PCR assay to be a rapid, sensitive and uniquely specific method for identification of *Helicobacter pylori* from various sources.

Example 2

Comparison of Multiplex PCR with Histology for Detection of *H. pylori*

Four to five gastric specimens were collected from 90 patients with dyspepsia symptoms undergoing endoscopy in Evanston Northwestern Healthcare. One specimen was sent to the clinical laboratory for the histology study performed by an expert clinical pathologist. The other two or three specimens were collected for DNA extraction and the one-step multiplex PCR was performed as described in Example 1. For the multiplex PCR analysis, a specimen was considered positive for *H. pylori* if 5 out of 10 DNA fragments or both DNA fragments from 2 out of the 5 loci were amplified.

As disclosed in Example 1, positive results were obtained in 68% (61/90) with multiplex PCR and 11% (10/90) with histology study (TABLE 1). The sensitivity and specificity was 16% and 100% for the histology method relative to multiplex PCR respectively (TABLE 1). The 10-primer pair-combination plus the internal control of each locus showed the multiplex PCR assay to be a rapid, sensitive and uniquely specific method for identification of *Helicobacter pylori* from various sources. Although false negative results may be obtained in the samples used for histology because the patchy *H. pylori* distribution present results still indicated that the disclosed multiplex PCR method is a highly specific and sensitive valuable method in the detection of *H. pylori* when an invasive diagnostic is justified.

Example 3

Food Products Tests for *H. pylori*

Eleven fresh raw chickens and 18 orders of ready-to-eat raw tuna meat were collected from local grocery and restaurants respectively. The samples were washed with enough volumes of phosphate buffered saline (PBS) and then the solution was concentrated to recover the bacteria. DNA was isolated by methods with some modifications and the disclosed novel one-step multiplex PCR detection system was used. For the multiplex PCR analysis, a specimen was considered positive for *H. pylori* if 5 out of 10 DNA fragments or both DNA fragments from 2 out of the 5 loci were amplified. *H. pylori* positive results were achieved in 36% (4/11) from fresh raw chickens and 44% (8/18) from ready-to-eat raw tuna meat by using the multiplex PCR detection system. Results indicated that the test samples obtained from local grocery and restaurants were contaminated with *H. pylori*. In spite of the difficulty in culturing *H. pylori* by currently available methods, this is evidence that some raw foods and ready-to-eat foods may take an important role in the transmission route of *H. pylori* infection in humans.

Materials and Methods

Multiplex PCR Design. A goal of the disclosed PCR method is to overcome false-negative results by amplifying more than one region at the same time because the possibility to amplify all or some of the selected DNA region is much higher when multiple regions are used rather than only one region. Moreover, the amplified DNA fragments can be confirmed using the internal control to rule out false-positives.

Primer Design. To design the multiplex PCR primers, several published primers were reviewed that are specific for *H. pylori* genes and the GenBank was searched. The urease genes (urea), 26 kDa protein antigen, Hpa A gene, 0.86 kb DNA fragment and DNA sequences of 16S ribosomal RNA were chosen as amplification targets.

For each locus, one forward primer was selected as the common primer (FC) and two reversed primers (R1 and R2) were selected in which R2 is inside the amplifying region of R1. In addition, these primers met the following criteria: 1) Tm, around 60° C., 2) G+C, about 50%, 3) length, 20-30 nt, 4) no dimer formations with other primers, 5) few mutations in the primer binding site after checking the published *H. pylori* DNA sequences, and 6) specific for *H. pylori*.

To better balance the primer mixture, the primers were divided into two groups: group A, with all the five FC primers and five R1 primers and group B, all the five FC primers with five R2 primers. Under these settings, 10 DNA fragments were amplified in two tubes at the same time.

*Helicobacter* pylon and other bacterial strains used. Three *H. pylori* stains ordered from American Type Culture Collection (Manassas, Va., USA): ATCC 43504, ATCC 700392 (26695) and ATCC 700824 (J99), and eleven common bacterial species, 1) *Escherichia coli*, 2) *Enterobacter cerogenes*, 3) *Enterobacter cloacae*, 4) *Enterococcus* spp., 5) Virdians Group, *Stereptococcus*, 6) *Pseudomonas aeroginosa*, 7) *Serratia* spp, 8) *Klebsiella pneumoniae*, 9) Methicillin resistant *Staphylococcus aureus*, 10) *Lactobacillus* spp. and 11) *Citrobacter* spp., which were isolated from clinical samples at Evanston Northwestern Healthcare, Evanston Hospital (Evanston, Ill.), were selected as templates to assay the accuracy, sensitivity, specificity, and reproducibility of the one-step multiple-nested PCR.

DNA Extraction. The DNA of *H. pylori* and other bacteria were isolated according to the published method with some modifications disclosed herein.

Buffers and Solutions: Ethanol, Potassium acetate (5 M), TE (pH 7.6), Cell lysis buffer: 10 mM Tris-Cl (pH 8.0), 0.05M EDTA (pH 8.0), 0.5% (w/v) SDS, 20 µg/ml DNase-free RNase. Other enzymes and buffers include DNase-free RNase (4 mg/ml), Proteinase K (20 mg/ml), DNA from mammalian tissue such as human gastric biopsy specimens containing *Helicobacter pylori* and other bacteria culture were extracted following the method disclosed herein.

The gastric tissue was ground with a small glass tissue grinding bar in a 1.5 ml eppendorf tube. For cultured *Helicobacter pylori* or other bacteria, one or two colonies were picked and introduced into a 1.5 ml tube with 50 µl TE. The tubes were heated at 100° C. for 5 minutes. Then 500 µl cell lysis buffer was added to the tubes followed by an addition of 3 µl of proteinase K solution to the lysate. The digest was incubated at 56° C. for 1 hour or for no longer than 16 hours at room temperature. The sample was allowed to cool to room temperature. Then, 200 µl of potassium acetate solution was added to the sample and the contents were mixed by vortexing the tube vigorously for 20 seconds.

The precipitated protein/SDS complex was pelleted by centrifugation at maximum speed (approximated 10,000 g) for 3 minutes at 4° C. in a microfuge. A pellet of protein was visible at the bottom of the microfuge tube after centrifugation. If no pellet was seen, the lysate was incubated for 5 minutes on ice and the centrifugation step was repeated. The clear supernatant was transferred to a fresh microfuge tube containing 500 µl of chloroform. The solution was mixed well and then centrifuged at maximum speed for 5 minutes at room temperature in a microfuge.

The upper aqueous phase was transferred to a fresh centrifuge tube and 900 µl of absolute ethanol was added to the tube. The tube was inverted several times and centrifuged at maximum speed for about 5 minutes at room temperature in a microfuge. The supernatant was removed by aspiration and 500 µl of 70% ethanol was added to the DNA pellet. The tube was inverted several times and centrifuged at maximum speed for 1 minute at room temperature in a microfuge.

The supernatant was removed without disturbing the pellet by aspiration and the DNA pellet was allowed to dry in air for about 15 minutes or until dry. The DNA pellet was redissolved in 50-100 µl of TE (pH 7.6).

Touch down PCR: The following PCR program was used for a touch down PCR: Initial denaturizing at 94° C. for 5 minutes, followed by the first 6 cycles at 94° C. for 40 seconds, 66° C. for 30 seconds and the annealing temperature is reduced from 66° C. to 61° C. by 1° C. per cycle, 72° C. for 50 seconds. Then approximately 36-40 cycles were repeated as follows: 94° C. 40 seconds, 56° C. 30 seconds, 72° C. 50 seconds, 72° C. 10 minutes, 4° C. hold. The PCR thermo cycle device used was of model Eppendorf Mastercycler 5333 (Eppendorf Scientific, Inc., Westbury, N.Y.).

Software used for primer design: DNASTAR, Lasergene® sequence analysis software, PrimerSelect 4.05 (DNASTAR, Inc., Madison, Wis. 53715).

Balancing the concentration of primer mix: Each primer solution was prepared at a concentration of 10 pmol/µl. Equal volume of the two primers for each locus was added to the PCR mix. The amplification of individual locus was tested and according to the results the concentration of primers was adjusted for subsequent experiments. Primers corresponding to multiple loci were mixed and the multiplex PCR was performed. Depending on the results, the final primer concentration was adjusted. For each primer, the concentration was about 0.05-0.1 pmol/µl for the multiplex PCR. The final concentrations of primers were tested under different PCR conditions to make sure that the primer mix would work well under a range of conditions, such as the amount of DNA template, polymerase, $Mg^{++}$ concentration, and a range of annealing temperatures and the like.

Immunomagnetic separation of *H. pylori* from human feces and DNA extraction: An exemplary immuno-separation and *H. pylori* DNA extraction is described in Monteiro et al., (2001), the disclosure is herein incorporated by reference. Stool specimens were suspended at 1.5:5 (wt/vol) for solid and semisolid samples and 1.5:5 (vol/vol) for liquid in phosphate-buffered saline and incubated overnight, under agitation at room temperature. The suspension was then filtered through three layers of cotton gauze and used for immunomagnetic separation of *H. pylori*. Briefly, magnetic uncoated beads were coated with rabbit anti-*H. pylori* immunoglobulin at a concentration of 5 µg of antibody for 1 Dynabeads according to the procedure recommended by Dynal. A 60-µl volume of coated Dynabeads was mixed with 1 ml of fecal suspension and incubated at 4° C. with continuous shaking for 2 h. The coated Dynabeads were recovered by magnetic force with a Dynalmagnet and then suspended in the lysis buffer of the QIAamp tissue kit for DNA extraction. Twenty microliters of a proteinase solution (20 mg/ml) was then added, followed by incubation at 56° C. for 2 h. A second buffer provided in the kit was added, and the sample was incubated at 70° C. for 10 min. Next, 200 µl of ethanol was added, and the suspension was loaded on the QIAamp spin column followed by a centrifugation at 6,000×g for 1 min. The QIAamp spin column was placed in a 2-ml collection microtube, and the tube containing the filtrate was discarded. The column material was washed twice (250 µl each) with the first washing buffer and twice (250 µl each) with the second washing buffer provided in the kit. Finally, the DNA was eluted with 100 µl of distilled water preheated to 70° C. (2×50 µl).

Amplification (Polymerase Chain Reaction, PCR). The template DNA was added to 20 µl of a reaction mixture containing 10 mM Tris-HCl (pH 8.3), 50 mM KCl, 1.6 mM $MgCl_2$, 0.001% (w/v) gelatin, 0.3 mM each deoxynucleotide, 0.05 µM each oligonucleotide primer. Immolase™ DNA polymerase (5.0 U; Bioline Ltd, London, UK) was used. The PCR was performed with a PCR thermal cycler (Marstercycler, Eppendorf Scientific Inc, Waterbury, N.Y., USA) and the PCR conditions were as follows: an initial denaturizing at 94° C. for 5 minutes, followed by the first 6 cycles at 94° C. for 40 seconds, 66° C. for 30 seconds and the annealing temperature is reduced from 66° C. to 61° C. by 1° C. per cycle, 72° C. for 50 seconds. The final extension step was at 72° C. for 10 min.

For example, two master mixes that each contain 4.0 µl of 5×PCR buffer, 1.0 µl of primer mix M1 or M2, 0.6 µl of 10 mM dNTPs and 1.0 µl of DNA polymerase (5U) were prepared. M1 contained for example F1/R1, F2/R2, F3/R3, F4/R4 and F5/R5, and M2 contained F1/RN1, F2/RN2, F3/RN3, F4/RN4 AND F5/RN5 (TABLE 2). Depending on the number of samples tested, the master mix was scaled-up. 1.0 ml of sample DNA isolated from the specimens were added to the master mix. The PCR was performed as described above.

Direct identification of cultured *H. Pylori*. For direct detection of *H. pylori* from culture, a colony was selected with a pipette tip and was mixed in 100 μl Tryptic Soy Broth or TE solution in a 0.5 ml test tube. Then 1 μl of the cell solution was directly added to a PCR tube with 19 μl PCR reaction mixture. Amplification was performed as disclosed herein.

Analysis of the multiplex PCR products. The analysis of PCR products was carried out by agarose gel electrophoresis, the PCR products were analyzed on a 2.0% agarose gel by electrophoresis of a 10 μl aliquot and stained with ethidium bromide and visualized by excitation under UV light. To conveniently compare the size of the amplified PCR products, previously amplified and confirmed PCR products from know H. pylori DNA were as used in addition to a commercial 100-bp DNA ladder.

Assaying the sensitivity of the one-step multiple-nested PCR. The sensitivity of the one-step multiple-nested PCR was investigated with serial dilutions of the H. pylori DNA, followed by amplification with the one-step multiple-nested PCR in the conditions disclosed herein.

Assaying the specificity of the one-step multiple-nested PCR. To test the specificity of the multiplex PCR assay, 11 bacterial species were chosen, which included: 1) Escherichia coli, 2) Enterobacter aerogenes, 3) Enterobacter cloacae, 4) Enterococcus AP, 5) Virdians Group, Stereptococcus, 6) Pseudomonas aeruginosa, 7) Serratia species, 8) Klebsiella pneumoniae, 9) methicillin resistant Staphylococcus aureus, 10) Lactobacillus spp. and 11) Citrobacter spp. as templates. The PCR was performed in the conditions described for system 2 (two tubes with five FC primers and five R primers each) along with H. pylori J99 as a positive control.

Comparing the CLOtest and histology method. Ninety stomach biopsy samples were collected from the patients with dyspepsia symptoms undergoing endoscopy in Evanston Northwestern Healthcare (informed consent was obtained). To overcome the problem of patchy H. pylori distribution (so that the organism is not captured in the tested tissue sample), the same gastric specimen was used for both CLOtest and PCR assay. Standard CLOtest methods were used. The CLOtest was performed first and after obtaining the results (waiting from about 20 minutes to 24 hours), specimens were collected from the CLOtest plates and DNA was isolated using standard DNA extraction procedures and the one-step multiplex PCR was performed. Other specimens were sent to the clinical laboratory for the histology study performed by an expert clinical pathologist.

TABLE 1

Sensitivity and Specificity of CLOtest and Histology relative to Multiplex PCR method.

| | Multiplex PCR | | | | |
|---|---|---|---|---|---|
| | N | (+) | (−) | Sensitivity | Specificity |
| CLOtest | | | | | |
| (+) | 39 | 38 | 1 | 38/61 = 0.62 | 28/29 = 0.97 |
| (−) | 51 | 23 | 28 | | |
| Total | 90 | 61 | 29 | | |
| Histology | | | | | |
| (+) | 10 | 10 | 0 | 10/61 = 0.16 | 29/29 = 1.0 |
| (−) | 80 | 51 | 29 | | |
| Total | 90 | 61 | 29 | | |

TABLE 2

Characteristics of primers and amplicons from five loci in H. pylori (SEQ ID NOS 6-20, respectively, in order of appearance)--

| Locus | Primer | 5'-3' Sequence[c] | Length/$T_m$ °C | | Amplicon Size[a] | H. pylori 26695 (position)[b] |
|---|---|---|---|---|---|---|
| 0.86 kb | F1 | AACGC CGTGA GTTCG TCGTA TCG | 23 | 61.9 | | 80650-80628 |
| (ureC | R1 | CATAT AGCCG CTTTT TCTGG TGTCT TTA | 28 | 59.2 | 706 bp | 79945-79972 |
| and prfA) | RN1 | CCTCA CGCCA TCAGT CCCAA AAAT | 24 | 61.9 | 574 bp | 80077-80100 |
| Ure A | F2 | TGATA GGCAA GCAGA CAACG AA | 22 | 56.3 | | 77351-77330 |
| gene | R2 | GATGT GTGTG TCAAT ACCAC CAGC | 24 | 62 | 526 bp | 76826-76849 |
| | RN2 | GCAGG ACCCA CGCTA AGATT GT | 22 | 57 | 465 bp | 76887-76908 |
| 16S | F3 | CAGGT CGCCT TCGCA ATGAG TA | 22 | 57.2 | | 1511958-1511937 |
| rRNA | R3 | ACGGG AGGCA GCAGT AGGGA ATA | 23 | 59.8 | 371 bp | 1512284-1512306 |
| | RN3 | GCCGC GTGGA GGATG AAGGT | 20 | 60.0 | 315 bp | 1512232-1512251 |
| 26 kDA | F4 | TCATG CCTTT ATCGC CTTTT CTCC | 24 | 59.5 | | 1645764-1645741 |
| | R4 | GTGGA AAAAG GCGGT ATCGG TCAA | 24 | 61.9 | 277 bp | 1645488-1645511 |
| | RN4 | CGATC GCTTT GAGAG GTGCT TTTT | 24 | 59.8 | 183 bp | 1645582-1645603 |

TABLE 2-continued

Characteristics of primers and amplicons from five loci in *H. pylori*
(SEQ ID NOS 6-20, respectively, in order of appearance)--

| Locus | Primer | 5'-3' Sequence[c] | Length/T<sub>m</sub> °C | Amplicon Size[a] | *H. pylori* 26695 (position)[b] |
|---|---|---|---|---|---|
| Hpa A | F5 | CTAGA GCCTA TGAGT GGGGA ATCTT T | 26  58.0 | | 854235-854210 |
| | R5 | ATCCG TTCCC TTAAC CATAG TGCT | 24  58.0 | 138 bp | 854098-854121 |
| | RN5 | TGCTA ACTAA CCCCC CGCTA TGGC | 24  57.2 | 118 bp | 854118-854141 |

[a]The "F" primers serve common to the "R" and "RN" primers. "RN" primers refer to the nested internal primers.
[b]position refers to the beginning and end of primer sequences in *H. pylori* 26695 genome (GenBank accession number AE000511.1).
[c]bold letter denotes mutations in the published sequence of *H. pylori*.

We claim:

1. A method of detecting *Helicobacter pylori* in a specimen, the method comprising:
   (a) performing a multiplex polymerase chain reaction, wherein a plurality of DNA fragments representing a plurality of loci in *Helicobacter pylori* are amplified by a plurality of forward and reverse primers, wherein for each pair of forward and reverse primer, a primer is internal, the primers selected from the group consisting of

AACGC CGTGA GTTCG TCGTA TCG (SEQ ID NO: 6),

CATAT AGCCG CTTTT TCTGG TGTCT TTA (SEQ ID NO: 7),

CCTCA CGCCA TCAGT CCCAA AAAT (SEQ ID NO: 8),

TGATA GGCAA GCAGA CAACG AA (SEQ ID NO: 9),

GATGT GTGTG TCAAT ACCAC CAGC (SEQ ID NO: 10),

GCAGG ACCCA CGCTA AGATT GT (SEQ ID NO: 11),

CAGGT CGCCT TCGCA ATGAG TA (SEQ ID NO: 12),

ACGGG AGGCA GCAGT AGGGA ATA (SEQ ID NO: 13),

GCCGC GTGGA GGATG AAGGT (SEQ ID NO: 14),

TCATG CCTTT ATCGC CTTTT CTCC (SEQ ID NO: 15),

GTGGA AAAAG GCGGT ATCGG TCAA (SEQ ID NO: 16),

CGATC GCTTT GAGAG GTGCT TTTT (SEQ ID NO: 17),

CTAGA GCCTA TGAGT GGGGA ATCTT T (SEQ ID NO: 18),

ATCCG TTCCC TTAAC CATAG TGCT (SEQ ID NO: 19), and

TGCTA ACTAA CCCCC GCTA TGGC (SEQ ID NO: 20); and (b) determining that a specimen is positive for *Helicobacter pylori* if a number of amplified fragments is sufficient to detect *Helicobacter pylori* in the specimen.

2. The method of claim 1, wherein the plurality of loci is selected from the group consisting of DNA sequences of a 0.86 kb DNA fragment, Urea A gene, 16S rRNA, a DNA sequence encoding a 26 kDa antigen, and Hpa A gene, whose nucleotide sequences are listed in FIG. 7.

3. A method for detecting *Helicobacter pylori* in a specimen, the method comprising:
(a) performing a multiplex polymerase chain reaction, wherein a first set of primers amplify a first set of DNA fragments from a *Helicobacter pylori* genomic sequence and a second set of primers amplify a second set of DNA fragments from a *Helicobacter pylori* genomic sequence that are internal to the first set of DNA fragments and wherein amplification is simultaneous, the primers selected from the group consisting of

AACGC CGTGA GTTCG TCGTA TCG (SEQ ID NO: 6),

CATAT AGCCG CTTTT TCTGG TGTCT TTA (SEQ ID NO: 7),

CCTCA CGCCA TCAGT CCCAA AAAT (SEQ ID NO: 8),

TGATA GGCAA GCAGA CAACG AA (SEQ ID NO: 9),

GATGT GTGTG TCAAT ACCAC CAGC (SEQ ID NO: 10),

GCAGG ACCCA CGCTA AGATT GT (SEQ ID NO: 11),

CAGGT CGCCT TCGCA ATGAG TA (SEQ ID NO: 12),

ACGGG AGGCA GCAGT AGGGA ATA (SEQ ID NO: 13),

GCCGC GTGGA GGATG AAGGT (SEQ ID NO: 14),

TCATG CCTTT ATCGC CTTTT CTCC (SEQ ID NO: 15),

GTGGA AAAAG GCGGT ATCGG TCAA (SEQ ID NO: 16),

CGATC GCTTT GAGAG GTGCT TTTT (SEQ ID NO: 17),

CTAGA GCCTA TGAGT GGGGA ATCTT T (SEQ ID NO: 18),

ATCCG TTCCC TTAAC CATAG TGCT (SEQ ID NO: 19), and

TGCTA ACTAA CCCCC CGCTA TGGC (SEQ ID NO: 20); and (b) determining that a specimen is positive for *Helicobacter pylori* if a number of amplified fragments is sufficient to detect the bacteria in the specimen.

4. A method for detecting *Helicobacter pylori* in a specimen, the method comprising:
(a) performing a multiplex polymerase chain reaction, wherein
(i) a first DNA fragment comprising a *Helicobacter pylori* genomic sequence is amplified by a first primer pair and an internal segment of the first DNA fragment is amplified by a second primer pair,
(ii) a second DNA fragment from a *Helicobacter pylori* genomic sequence is amplified by a third primer pair and an internal segment of the second DNA fragment is amplified by a fourth primer pair wherein the amplification is simultaneous, wherein the primer pairs are selected from the group consisting of:

AACGC CGTGA GTTCG TCGTA TCG (SEQ ID NO: 6),

CATAT AGCCG CTTTT TCTGG TGTCT TTA (SEQ ID NO: 7),

CCTCA CGCCA TCAGT CCCAA AAAT (SEQ ID NO: 8),

TGATA GGCAA GCAGA CAACG AA (SEQ ID NO: 9),

GATGT GTGTG TCAAT ACCAC CAGC (SEQ ID NO: 10),

GCAGG ACCCA CGCTA AGATT GT (SEQ ID NO: 11),

-continued

CAGGT CGCCT TCGCA ATGAG TA (SEQ ID NO: 12),

ACGGG AGGCA GCAGT AGGGA ATA (SEQ ID NO: 13),

GCCGC GTGGA GGATG AAGGT (SEQ ID NO: 14),

TCATG CCTTT ATCGC CTTTT CTCC (SEQ ID NO: 15),

GTGGA AAAAG GCGGT ATCGG TCAA (SEQ ID NO: 16),

CGATC GCTTT GAGAG GTGCT TTTT (SEQ ID NO: 17),

CTAGA GCCTA TGAGT GGGGA ATCTT T (SEQ ID NO: 18),

ATCCG TTCCC TTAAC CATAG TGCT (SEQ ID NO: 19), and

TGCTA ACTAA CCCCC CGCTA TGGC (SEQ ID NO: 20); and (b) determining that a specimen is positive for *Helicobacter pylori* if a number of amplified fragments is sufficient to detect the bacteria in the specimen.

5. The method of claim 3, wherein the multiplex polymerase chain reaction with the first set of primers is performed separately from the multiplex polymerase chain reaction with the second set of primers.

6. The method of claim 3, wherein the first set of primers and the second set of primers amplify a total of ten fragments representing five loci in the *Helicobacter pylori* sequence.

7. The method of claim 1, wherein the *Helicobacter pylori* locus is selected from the group consisting of coding, non-coding, exons, introns, and regulatory regions.

8. The method of claim 1, wherein the primers comprise the following characteristics:
(a) about twenty to thirty bases long;
(b) melting temperature of about 60° C.;
(c) GC content of about fifty percent;
(d) minimal dimer formation; and
(e) low frequency of mutations in the primer binding site.

9. The method of claim 4, wherein the multiplex polymerase chain reaction is performed with an isolated bacterial DNA.

10. The method of claim 9, wherein the bacterial DNA is isolated from a clinical sample.

11. The method of claim 10, wherein the clinical sample is selected from the group consisting of gastrointestinal tract tissue, stool, urine, blood, saliva, mucus secretions, dental plaque, and other tissues capable of containing *Helicobacter pylori*.

12. The method of claim 4, wherein the multiplex polymerase chain reaction is performed directly with a biological sample.

13. The method of claim 12, wherein the biological sample is selected from the group consisting of cell culture, bacterial cell culture, gastrointestinal tract tissue, stool, urine, blood, saliva, mucus secretions, dental plaque, and other sample capable of containing *H. pylori*.

14. The method of claim 4, wherein the first primer pair and the second primer pair have a common primer.

15. The method of claim 4 further comprising performing a multiplex polymerase chain reaction, wherein up to ten DNA fragments representing five *Helicobacter pylori* loci are amplified by fifteen primers, the ten DNA fragments representing five internal fragments.

16. The method of claim 15, wherein the fifteen primers comprise five forward and ten reverse primers.

17. The method of claim 15, wherein a specimen is considered positive if at least fifty percent of all the DNA fragments or at least four DNA fragments representing two loci in *Helicobacter pylori* are amplified.

18. The method of claim 1, wherein a specimen is positive for *Helicobacter pylori* if at least fifty percent of all the DNA fragments or at least four DNA fragments representing two loci in *Helicobacter pylori* are amplified.

* * * * *

SEQUENCE LISTING

<160> NUMBER OF SEQ ID NOS: 20

<210> SEQ ID NO 1
<211> LENGTH: 706
<212> TYPE: DNA
<213> ORGANISM: Helicobacter pylori

<400> SEQUENCE: 1

```
catatagccg cttttctgg tgtctttacc gattagaatt ttattcgttt gagaatgttt      60
tttaaaatac aatccggcag caatgcctaa acgcatcaca aacatggggg tgagtttcac     120
ccctgcttta cccctcacgc catcagtccc aaaaattttc atcgttataa aataccttt     180
aaactatttt taatcaattt ttagatagaa ttatgccaaa ttttacatta caagggatt      240
aaaacaaggc tatggcaaat cataagtccg cagaaaagcg aatcagacag accattaaga     300
gaaccgaacg caacaggttc tataaaacta aaattaaaaa tatcattaaa gccgtgcgtg     360
aagccgttgc tgtcaatgat gtagcaaaag ctcaagagcg tttgaaaatc gctaataaag     420
agttgcataa atttgtcagc aagggggatt taagaaaaa caccgcttct aggaaagtct     480
caaggcttaa cgcttcagtg aaaaaaatcg ctctcgctta gttttgtggc gttttcaact     540
tcttttaagct cagtaatggg tttttattat tgggcttctt tttaagtttt gcgttttta     600
gattgttgta ttttttattc acatcttttt ataggtagtc tcgcatgtcc attctagccg     660
aaaagctttc ttccattctc aaacgatacg acgaactcac ggcgtt               706
```

<210> SEQ ID NO 2
<211> LENGTH: 526
<212> TYPE: DNA
<213> ORGANISM: Helicobacter pylori

<400> SEQUENCE: 2

```
gatgtgtgtg tcaataccac cagcagttac gatcaaacct tcaccggcta aggcttcagt      60
agcaggacct acgctaagat tgttttaac gccatcttgc atgtctttgt taccgccttt     120
accaatgcca gcgattttgc catctttaat accaatatcc gctttataaa taccggtgta     180
atccacgatt aaagcgttag tgatgattag atccaattct tctttgctag ggttgttgga     240
ttggctcatg ccttctctca gggttttacc gccaccgaat ttaagctctt cgccataaat     300
ggtgtagtca tgttctactt cagcgatcaa gtctgtatcg cccaatctca ctttatcgcc     360
tgtagtaggg ccatacatag aaacatattc ttttctgcta atcttttca tttcttactc     420
cttaattgtt tttacatagt tgtcatcgct tttagcgcca tgaaaccac gctctttagc     480
```
tctgtgtaaa gcaattttt tgctttcgtt gtctgcttgc ctatca 526

<210> SEQ ID NO 3
<211> LENGTH: 370
<212> TYPE: DNA
<213> ORGANISM: Helicobacter pylori

<400> SEQUENCE: 3
acgggaggca gcagtaggga atattgctca atggggggaaa ccctgaagca gcaacgccgc 60
gtggaggatg aaggtttag gattgtaaac tccttttgtt agagaagata atgacggtat 120
ctaacgaata agcaccggct aactccgtgc cagcagccgc ggtaatacgg agggtgcaag 180
cgttactcgg aatcactggg cgtaaagagc gcgtaggcgg atagtcagt caggtgtgaa 240 atcctatggc ttaaccatag aactgcattt gaaactacta ttctagagtg tgggagaggt 300
aggtggaatt cttggtgtag gggtaaaatc cgtagagatc aagaggaata ctcattgcga 360
aggcgacctg 370

<210> SEQ ID NO 4
<211> LENGTH: 277
<212> TYPE: DNA
<213> ORGANISM: Helicobacter pylori

<400> SEQUENCE: 4
gtagaaaaag gcggtattgg tcaagtaact ttccctatgg tggctgatat taccaaaagc 60
atttctagag actatgatgt gttgtttgaa gaagcgatcg cttttgagagg agcttttttg 120 attgacaaaa acatgaaagt aaggcatgcg gtgatcaatg acttaccatt aggcagaaat 180
gcagatgaaa tgcttcgcat ggtggacgct ctcttacact ttgaagaaca tggtgaagtt 240
tgcccagcag gttggagaaa aggcgataaa ggcatga 277

<210> SEQ ID NO 5
<211> LENGTH: 138
<212> TYPE: DNA
<213> ORGANISM: Helicobacter pylori

<400> SEQUENCE: 5
atccgttccc ttaaccatag tgctaactaa ccccccgcta tggcttgaat gggtggtttt 60
taagaatttt tcttgaatgt ccaactcgct caaatccatc gtaaaagaat ccaaagattc 120
cccactcata ggctctag 138

<210> SEQ ID NO 6
<211> LENGTH: 23
<212> TYPE: DNA
<213> ORGANISM: Helicobacter pylori

<400> SEQUENCE: 6
aacgccgtga gttcgtcgta tcg 23

<210> SEQ ID NO 7
<211> LENGTH: 28
<212> TYPE: DNA
<213> ORGANISM: Helicobacter pylori

<400> SEQUENCE: 7
catatagccg cttttctgg tgtcttta 28

<210> SEQ ID NO 8
<211> LENGTH: 24

```
<212> TYPE: DNA
<213> ORGANISM: Helicobacter pylori

<400> SEQUENCE: 8
cctcacgcca tcagtcccaa aaat                                              24

<210> SEQ ID NO 9
<211> LENGTH: 22
<212> TYPE: DNA
<213> ORGANISM: Helicobacter pylori

<400> SEQUENCE: 9
tgataggcaa gcagacaacg aa                                                22

<210> SEQ ID NO 10
<211> LENGTH: 24
<212> TYPE: DNA
<213> ORGANISM: Helicobacter pylori

<400> SEQUENCE: 10
gatgtgtgtg tcaataccac cagc                                              24

<210> SEQ ID NO 11
<211> LENGTH: 22
<212> TYPE: DNA
<213> ORGANISM: Helicobacter pylori

<400> SEQUENCE: 11
gcaggaccca cgctaagatt gt                                                22

<210> SEQ ID NO 12
<211> LENGTH: 22
<212> TYPE: DNA
<213> ORGANISM: Helicobacter pylori

<400> SEQUENCE: 12
caggtcgcct tcgcaatgag ta                                                22

<210> SEQ ID NO 13
<211> LENGTH: 23
<212> TYPE: DNA
<213> ORGANISM: Helicobacter pylori

<400> SEQUENCE: 13
acgggaggca gcagtaggga ata                                               23

<210> SEQ ID NO 14
<211> LENGTH: 20
<212> TYPE: DNA
<213> ORGANISM: Helicobacter pylori

<400> SEQUENCE: 14
gccgcgtgga ggatgaaggt                                                   20

<210> SEQ ID NO 15
<211> LENGTH: 24
<212> TYPE: DNA
<213> ORGANISM: Helicobacter pylori

<400> SEQUENCE: 15
tcatgccttt atcgcctttt ctcc                                              24

<210> SEQ ID NO 16
```

```
<211> LENGTH: 24
<212> TYPE: DNA
<213> ORGANISM: Helicobacter pylori

<400> SEQUENCE: 16
gtggaaaaag gcggtatcgg tcaa                                          24

<210> SEQ ID NO 17
<211> LENGTH: 24
<212> TYPE: DNA
<213> ORGANISM: Helicobacter pylori

<400> SEQUENCE: 17
cgatcgcttt gagaggtgct tttt                                          24

<210> SEQ ID NO 18
<211> LENGTH: 26
<212> TYPE: DNA
<213> ORGANISM: Helicobacter pylori

<400> SEQUENCE: 18
ctagagccta tgagtgggga atcttt                                        26

<210> SEQ ID NO 19
<211> LENGTH: 24
<212> TYPE: DNA
<213> ORGANISM: Helicobacter pylori

<400> SEQUENCE: 19
atccgttccc ttaaccatag tgct                                          24

<210> SEQ ID NO 20
<211> LENGTH: 24
<212> TYPE: DNA
<213> ORGANISM: Helicobacter pylori

<400> SEQUENCE: 20
tgctaactaa cccccgcta tggc                                           24
```